United States Patent
Shlomo

(10) Patent No.: US 6,272,371 B1
(45) Date of Patent: *Aug. 7, 2001

(54) BEND-RESPONSIVE CATHETER

(75) Inventor: Ben-Haim Shlomo, Haifa (IL)

(73) Assignee: Biosense Inc., New Brunswick, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,932

(22) PCT Filed: Dec. 31, 1997

(86) PCT No.: PCT/IL97/00449
§ 371 Date: Feb. 22, 1999
§ 102(e) Date: Feb. 22, 1999

(87) PCT Pub. No.: WO98/29033
PCT Pub. Date: Jul. 9, 1998

Related U.S. Application Data

(60) Provisional application No. 60/034,703, filed on Jan. 3, 1997, and provisional application No. 60/034,704, filed on Jan. 3, 1997.

(51) Int. Cl.[7] .......................................... A61B 5/05
(52) U.S. Cl. .............................. 600/424; 128/899
(58) Field of Search ..................... 600/117, 424; 128/899; 607/122

(56) References Cited

U.S. PATENT DOCUMENTS

| | | |
|---|---|---|
| 4,570,354 | 2/1986 | Hindes .................................. 33/534 |
| 4,651,436 | 3/1987 | Gaal ..................................... 33/533 |
| 4,921,482 | 5/1990 | Hammerslag et al. ................. 604/95 |
| 4,982,725 | 1/1991 | Hibino et al. ........................... 128/4 |
| 5,042,486 | 8/1991 | Pfeiler et al. ......................... 128/653 |
| 5,253,647 | 10/1993 | Takahashi et al. ................. 128/653.1 |
| 5,269,289 | 12/1993 | Takehana et al. ....................... 128/4 |
| 5,273,025 | 12/1993 | Sakiyama et al. ....................... 128/6 |
| 5,295,484 | 3/1994 | Marcus et al. ................... 128/660.03 |
| 5,295,486 | 3/1994 | Wollschlager et al. ......... 128/661.01 |
| 5,391,199 | 2/1995 | Ben-Haim ............................ 607/122 |
| 5,425,367 | 6/1995 | Shapiro et al. .................... 128/653.1 |
| 5,465,717 | 11/1995 | Imran et al. .......................... 128/642 |
| 5,471,982 | 12/1995 | Edwards et al. ..................... 128/642 |
| 5,558,073 | 9/1996 | Pomeranz et al. ................... 128/642 |
| 5,617,857 | 4/1997 | Chader et al. ..................... 128/653.1 |

FOREIGN PATENT DOCUMENTS

| | | |
|---|---|---|
| WO 92/03090 | 3/1992 | (WO) . |
| WO 94/00050 | 1/1994 | (WO) . |
| WO 95/04938 | 2/1995 | (WO) . |
| WO 95/19738 | 7/1995 | (WO) . |
| WO 96/05768 | 2/1996 | (WO) . |
| WO 97/24983 | 7/1997 | (WO) . |

Primary Examiner—Ruth S. Smith
(74) Attorney, Agent, or Firm—Louis J. Capezzuto

(57) ABSTRACT

This invention is an invasive probe apparatus including flexible elongate probe (20) having a distal portion adjacent to a distal end (22) thereof for insertion into the body of a subject, which portion assumes a predetermined curve form when a force is applied thereto. First and second sensors (28, 30) are fixed to the distal portion of the probe (20) in known positions relative to the distal end (22), which sensors generate signals responsive to bending of the probe. Signal processing circuitry (36) receives the bend responsive signals and processes them to find position and orientation coordinates of at least the first sensor (28), and to determine the locations of a plurality of points along the length of the distal portion of the probe.

30 Claims, 3 Drawing Sheets

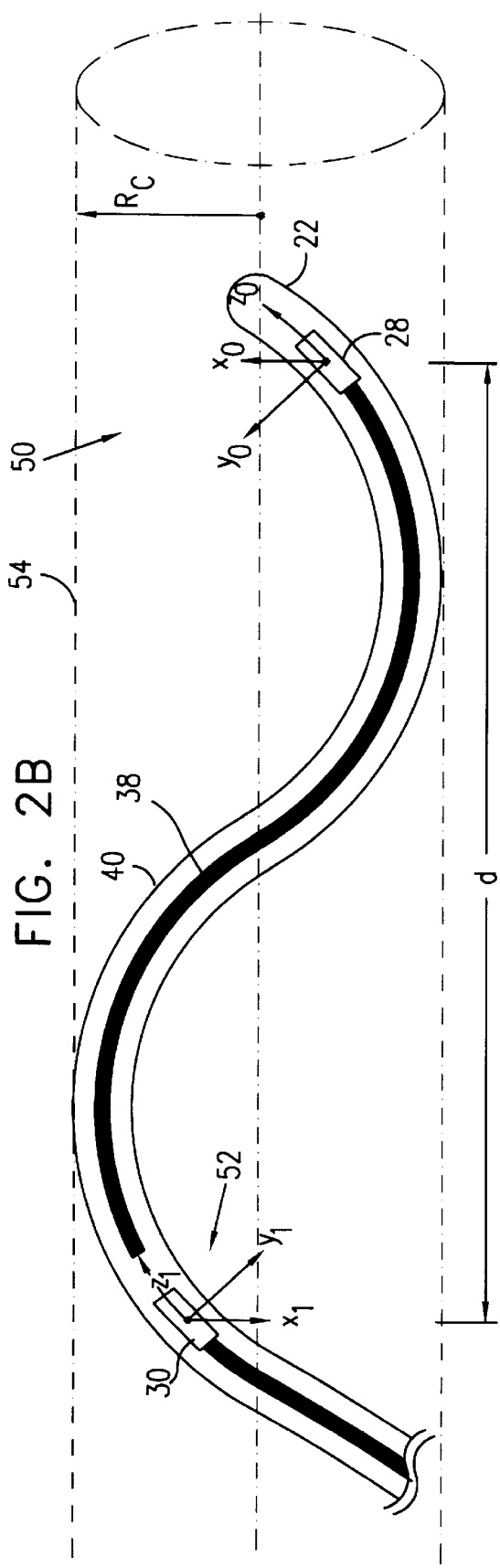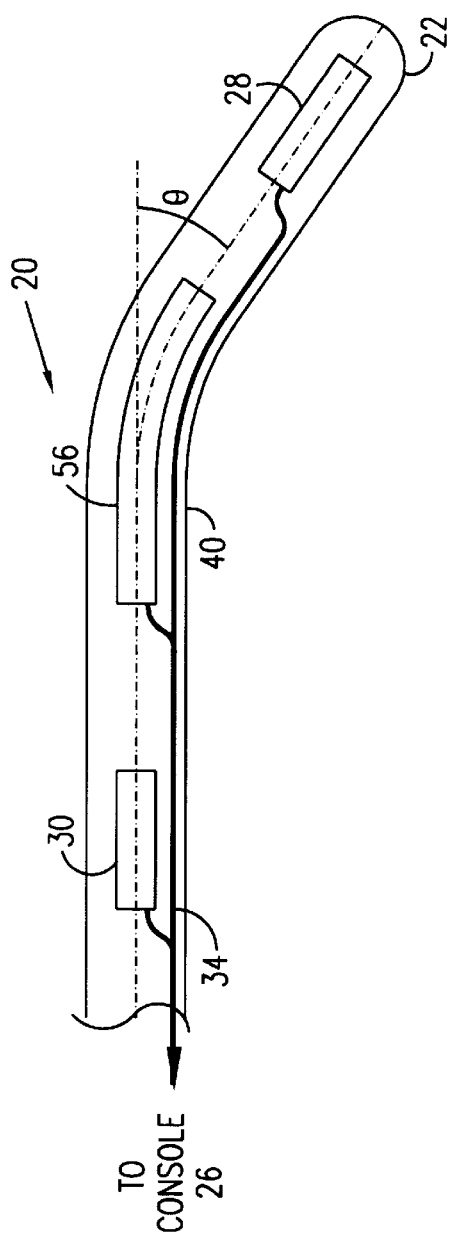

BEND-RESPONSIVE CATHETER

RELATED APPLICATIONS

This application claims the benefit of U.S. Provisional Patent Applications Nos. 60/034,703 and 60/034,704, filed Jan. 3, 1997, which are assigned to the assignee of the present patent application and incorporated herein by reference.

FIELD OF THE INVENTION

The present invention relates generally to cardiac diagnostic and therapeutic systems, and specifically to invasive medical probes that may be used to map the interior surfaces of the heart.

BACKGROUND OF THE INVENTION

Position-responsive cardiac catheters are known in the art. Such catheters are generally inserted percutaneously and fed through one or more major blood vessels into a chamber of the heart. A position-sensing device in the catheter, typically near the catheter's distal end, gives rise to signals that are used to determine the position of the device (and hence of the catheter) relative to a frame of reference that is fixed either externally to the body or to the heart itself. The position-sensing device may be active or passive and may operate by generating or receiving electrical, magnetic or ultrasonic energy fields or other suitable forms of energy known in the art.

U.S. Pat. No. 5,391,199, which is incorporated herein by reference, describes a position-responsive catheter comprising a miniature sensor coil contained in the catheter's distal end. The coil generates electrical signals in response to externally-applied magnetic fields, which are produced by field-generator coils placed outside the patient's body. The electrical signals are analyzed to determine three-dimensional position coordinates of the coil.

PCT patent publication number WO96/05768, filed Jan. 24, 1995, which is assigned to the assignee of the present application and whose disclosure is incorporated herein by reference, describes a position-responsive catheter comprising a plurality of miniature, preferably non-concentric sensor coils fixed in its distal end. As in the U.S. Pat. No. 5,391,199 patent, electrical signals generated by these coils in response to an externally-applied magnetic field are analyzed so as to determine, in a preferred embodiment, six-dimensional position and orientation coordinates of the coils.

Multiple position-sensing devices may be placed in a known, mutually-fixed spatial relation at or adjacent to the distal end of a catheter, as described, for example, in PCT patent application no. PCT/IL97/00009, which is assigned to the assignee of the present application and whose disclosure is incorporated herein by reference. This application describes a catheter having a substantially rigid structure at its distal end, to which one or more position sensors are fixed. The sensors are used to determine the position and orientation of the structure, preferably for use in mapping electrical activity in the heart. Although the structure itself is substantially rigid, the remainder of the catheter is generally flexible, and the position sensors do not provide coordinate information regarding any points on the catheter proximal to the structure.

PCT publication WO95/04938, which is also incorporated herein by reference, describes a miniature magnetic field sensor coil and method of remotely determining the coil's location. The sensor coil may be used to determine the spatial configuration or course of flexible endoscope within the body of a subject in one of two ways: (1) By passing the coil through an internal lumen of the endoscope, for example, the endoscope's biopsy tube, and externally tracking the coil's location while the endoscope is held stationary; or (2) By distributing a plurality of the coils, preferably about a dozen, along the length of the endoscope and determining all of the coils' locations. The position coordinates determined with respect to each location of the coil (when a single coil is used) or to all the coils (when the plurality of coils are used) are taken together to interpolatively reconstruct the spatial configuration of the endoscope within the intestines of the subject, for example, and thereby estimate the corresponding spatial configuration of the intestines.

The accuracy of this endoscope in estimating the spatial configuration of the intestines depends on having a relatively large number of position measurements and/or of coils. Passing the coil (or other sensor element) through a lumen in the endoscope is time consuming and physically not practical for use in thin probes, such as cardiac catheters that must be passed through blood vessels. Using a large number of coils, however, undesirably increases the weight and cost of the catheter and reduces its flexibility.

U.S. Pat. No. 5,042,486, whose disclosure is further incorporated herein by reference, describes a method of locating a catheter within the body of a subject, generally within a blood vessel, by tracking the position of an electromagnetic or acoustic transmitter or receiver in the tip of the catheter. The position readings are registered with a previously acquired X-ray image of the blood vessel. This method is practical, however, only when the catheter is moving within a vessel or other physiological structure that defines a narrow channel within which the catheter's movement is constrained.

PCT publication WO 92/03090, whose disclosure is also incorporated herein by reference, describes a probe system, such as an endoscope, including sensing coils mounted at spaced positions along the probe. An array of antennas in a vicinity of the probe are driven by AC electrical signals, so as to induce corresponding voltage signals in the sensing coils. These signals are analyzed to determine three-dimensional coordinates of the coils. The locations of points along the probe, intermediate a pair of the sensing coils, may be determined by interpolation between the respective coordinates of the coils.

SUMMARY OF THE INVENTION

It is an object of the present invention to provide a generally flexible catheter, for insertion into the body of a subject, wherein the course and/or position of the catheter within the body are determined using a minimal number of sensors fixed to the catheter.

It is a further object of the present invention to provide a catheter having a distal portion that assumes a predetermined shape or curvature, dependent on a force is applied thereto, and a method of determining the course of the distal portion within the body.

In one aspect of the present invention, the entire course of the distal portion is determined by measuring position coordinates of two points on the portion and using the coordinates to find the shape or curvature of the portion.

In another aspect of the present invention, the entire course of the distal portion is determined by measuring position coordinates of a point on the portion and measuring the curvature of the portion.

It is yet another object of the current invention that the course of the catheter may be determined within body cavities in which the catheter is free to move in three dimensions, and not only within constraining lumens as in the prior art.

In preferred embodiments of the present invention, a flexible catheter, having a distal end for insertion into the body of a subject, comprises first and second sensors, fixed at known, respective positions along a generally distal portion of the length of the catheter, in a known relation to one another and to the distal end. The distal portion of the catheter is sufficiently resilient so as to assume a predetermined, curved form when a force is applied thereto. At least one of the sensors is a position sensor, which generates signals responsive to the position coordinates thereof. The outputs of the first and second sensors are processed jointly to determine the curvature of the portion of the catheter, so as to find the positions of a plurality of points along the length of the distal portion, inside the subject's body.

Preferably, the at least one position sensor comprises a magnetic-field-responsive coil, as described in the above-mentioned U.S. Pat. No. 5,391,199 patent, or more preferably, a plurality of such coils, as described in the above-mentioned PCT publication WO96/05768. The plurality of coils enables six-dimensional position and orientation coordinates to be determined. Alternatively, any suitable position sensor known in the art may be used, such as electrical, magnetic or acoustic sensors.

In some preferred embodiments of the present invention, both the first and second sensors comprise position sensors, preferably of the type described above with reference to the PCT publication, which allows their six-dimensional coordinates to be determined. The coordinates of the second sensor, relative to those of the first sensor, are determined and taken together with other, known information pertaining to curvature of the catheter. As will be described below, this information is used to find the positions of a plurality of points along the length of the catheter in a vicinity of the first and second sensors.

In some of these preferred embodiments, the catheter has an elasticity that is generally constant over at least a portion of its length, for example, due to internal reinforcement of the catheter with a resilient longitudinal member, as is known in the art. In this case, absent significant deformation of the catheter due to external forces, the known position and orientation coordinates of the first and second position-sensing elements, determined as described above, are sufficient to establish the curvature of catheter intermediate the elements.

In other preferred embodiments of the present invention, the first sensor comprises a position sensor, as described above, while the second sensor comprises a bend sensor, which generates signals responsive to a bend radius of the catheter in a vicinity thereof. Preferably, the bend sensor comprises one or more piezoelectric sensors, as are known in the art, which generate electrical signals proportional to a force or torque exerted thereon when the catheter bends. Alternatively, the bend sensor may comprise one or more strain sensors, as are known in the art. Further alternatively, the bend sensor may comprise a fiberoptic sensor fixed in the catheter, wherein the bend radius is determined by measuring the loss and/or back-reflection of light in an optical fiber, as is known in the art.

Further alternatively, the catheter may include a user-controlled bending mechanism, such as a pull-wire or other mechanism known in the art, or bending mechanisms of other types as described in PCT patent application no. PCT/IL97/00159, which is assigned to the assignee of the present invention, and whose disclosure is incorporated by reference. Preferably, the bending mechanism is calibrated, so that the bend radius of the catheter in a vicinity thereof is known, and is used in determining the positions of the plurality of points along the catheter.

In some preferred embodiments of the present invention, the catheter includes physiological sensors, such as electrophysiological sensing electrodes, or, additionally or alternatively, therapeutic devices, such as ablation electrodes, at some or all of the plurality of points along its length. Such embodiments are particularly useful, for example, in diagnosis and treatment of abnormal electrical conduction paths in the heart. Devices and methods for use in accordance with these preferred embodiments are further described in U.S. provisional patent application No. 60/034,704 which is assigned to the assignee of the present patent application, and whose disclosure is incorporated herein by reference.

Although preferred embodiments are described herein with reference to certain types of position and orientation sensors, the principles of the present invention may be implemented in catheters including other types and combinations of such sensors, as are known in the art. It is generally unnecessary to determine six-dimensional position and orientation coordinates of the sensors. It is sufficient, for example, that the first position sensor provide five-dimensional position and orientation data (to determine its three-dimensional translational coordinates and two-dimensional rotational azimuth and elevation), and the second position sensor provide three-dimensional position information. Under these conditions, the positions of the plurality of points along the catheter can be determined, as described above.

While the preferred embodiments of the present invention are generally described herein with reference to one or two position sensor and/or a single bend sensor, it will be appreciated that the inventive principles that they embody may be similarly applied to catheters, or other probes, having a plurality of position sensors and/or a plurality of bend sensors. Preferably, however, the number of such sensors is held to the minimum needed to achieve the desired accuracy of determination of the plurality of points along the length of the catheter, generally along the portion of the catheter adjacent the distal end thereof.

Furthermore, although the preferred embodiments described herein make reference to catheters, and particularly to intracardiac catheters, it will be appreciated that the principles of the present invention may similarly be applied to other types of flexible medical probes, such as endoscopes.

There is therefore provided, in accordance with a preferred embodiment of the present invention, invasive probe apparatus including:

a flexible, elongate probe, having a distal portion adjacent to a distal end thereof, for insertion into the body of a subject, which portion assumes a predetermined, curved form when a force is applied thereto;

first and second sensors, fixed to the distal portion of the probe in known positions relative to the distal end, which sensors generate signals responsive to bending of the probe; and signal processing circuitry, which receives the bend-responsive signals and processes them to find position and orientation coordinates of at least the first sensor and to determine the locations of a plurality of points along the length of the distal portion of the probe.

Preferably, the first sensor comprises three coils, which generate signals responsive to an externally-applied magnetic field.

Preferably, the probe has a generally constant elasticity over the length of the distal portion thereof and includes a resilient longitudinal member.

In some preferred embodiments of the present invention, the second sensor includes a position-sensing element, and the signal processing circuitry processes the signals generated by the second sensor to find position and orientation coordinates thereof.

Preferably, the position and orientation coordinates found by the signal processing circuitry include six-dimensional position and orientation coordinates.

In other preferred embodiments of the present invention, the second sensor includes a bend-sensing element, which generates signals responsive to a direction of bending of the probe.

Preferably, the bend-sensing, element includes at least one piezoelectric crystal, and more preferably, three such crystals, each crystal having an axis, wherein the axes are mutually orthogonal.

Alternatively, the bend-sensing element includes a fiberoptic sensor or a strain sensor.

Preferably, the signal processing circuitry determines a radius of curvature of the probe or, alternatively or additionally, a radius and a pitch of a helical form described by the probe.

Preferably, the probe comprises a deflection device within the distal portion thereof.

There is further provided, in accordance with a preferred embodiment of the present invention, a method for determining the course of an elongate, flexible probe inside the body of a subject, including:

finding position and orientation coordinates of a point on the probe;

measuring a bending angle of a portion of the probe adjacent to the point; and processing the position and orientation coordinates and the bending angle to determine the locations of a plurality of points along the length of a portion of the probe inside the body.

Preferably, finding position and orientation coordinates includes finding six-dimensional position and orientation coordinates.

Further preferably, measuring a bending angle includes finding position coordinates of an additional point on the probe.

Alternatively, measuring a bending angle comprises measuring a force associated with bending the probe.

Preferably, processing the position coordinates and the bending angle includes calculating a radius of curvature of the probe or, alternatively or additionally, calculating a radius of a helical path described by the probe.

The present invention will be more fully understood from the following detailed description of the preferred embodiments thereof, taken together with the drawings in which:

BRIEF DESCRIPTION OF THE DRAWINGS

FIG. 2B is a schematic illustration of a portion of the catheter shown in FIG. 1, in a second, twisted configuration, FIG. 3 is a schematic illustration showing a bend-responsive catheter, in accordance with another preferred embodiment of the present invention.

DETAILED DESCRIPTION OF PREFERRED EMBODIMENTS

Figure 1:
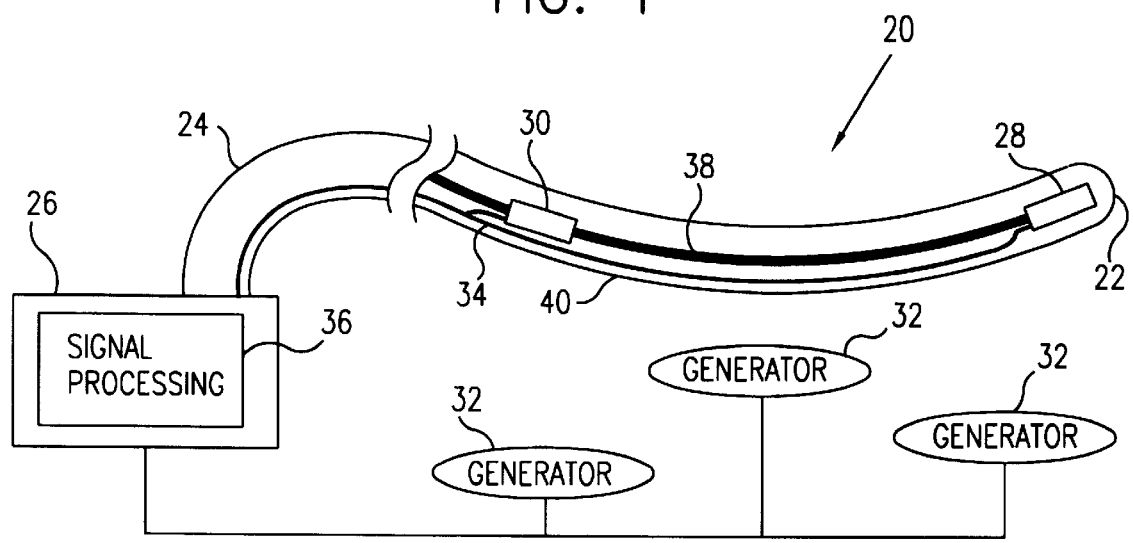
FIG. 1 is a schematic illustration of a bend-responsive catheter system, in accordance with a preferred embodiment of the present invention.

Reference is now made to FIG. 1, which illustrates a bend-responsive catheter 20, in accordance with a preferred embodiment of the present invention. Catheter 20 includes a distal end 22, which is preferably inserted in the heart of a subject, and a proximal end 24, which is coupled to a control console 26.

Adjacent to distal end 22, catheter 20 includes a first position-sensing element 28 and, proximal thereto, a second position-sensing element 30, which serves to enable determination of a bending angle of catheter 20, as will be described below. Preferably, each of elements 28 and 30 comprises three substantially orthogonal, non-concentric coils, as described in the above-mentioned PCT publication WO96/05768, which generate signals responsive to magnetic fields applied by field generators 32. These signals are conveyed via wires 34 to signal processing and computing circuitry 36 in console 26, which preferably also provides driver and control signals to generators 32. Circuitry 36 analyzes the signals, as further described in the PCT publication, in order to determine the six-dimensional translational and orientational coordinates of elements 28 and 30 in relation to a frame of reference established by generators 32.

Alternatively, it is sufficient that one of elements 28 and 30 comprise three such coils, and that the other of the elements comprise a single coil, as described in the above-mentioned U.S. Pat. No. 5,391,199 patent. As described in the patent, three-dimensional translational coordinates of the single-coil element are determined.

Further alternatively, sensors 28 and 30 may comprise other types and combinations of position sensors, known in the art. It is sufficient, for example, that element 28 be such as to enable determination of three-dimensional translational coordinates and two-dimensional angular elevation and azimuth coordinates with respect thereto, while three-dimensional coordinates are determined with respect to element 30. If bending of catheter 20 is constrained to a plane, as shown in FIG. 2A and described below, it is sufficient to determine two-dimensional coordinates of element 30.

Catheter 20 preferably includes a resilient longitudinal member 38, for example, a coil spring element, which is fixed within the catheter along a longitudinal axis thereof. Preferably, there is a sufficient distance between metal parts of member 38 and sensors 28 and 30 so that the metal parts do not significantly distort the magnetic fields at the sensors. Such distortion may be caused, for example, by eddy currents induced in the metal parts or by bending of the magnetic field lines by ferromagnetic materials. On account of member 38, catheter 20 has a generally constant elasticity over at least a portion 40 of its length, preferably extending at least from element 30, or from another point proximal thereto, out to distal end 22, or at least to element 28. Portion 40 of catheter 20 is preferably short enough, generally less that about 9 cm long, so that it is inserted entirely into a chamber of the heart with no more than a single bend in the portion. As a result, when portion 40 is bent, whereby element 30 is translationally displaced and orientationally rotated by a known angle relative to element 28, portion 40 will assume an arcuate or helical shape having a known radius of curvature, determined by the known angle.

Figure 2A:
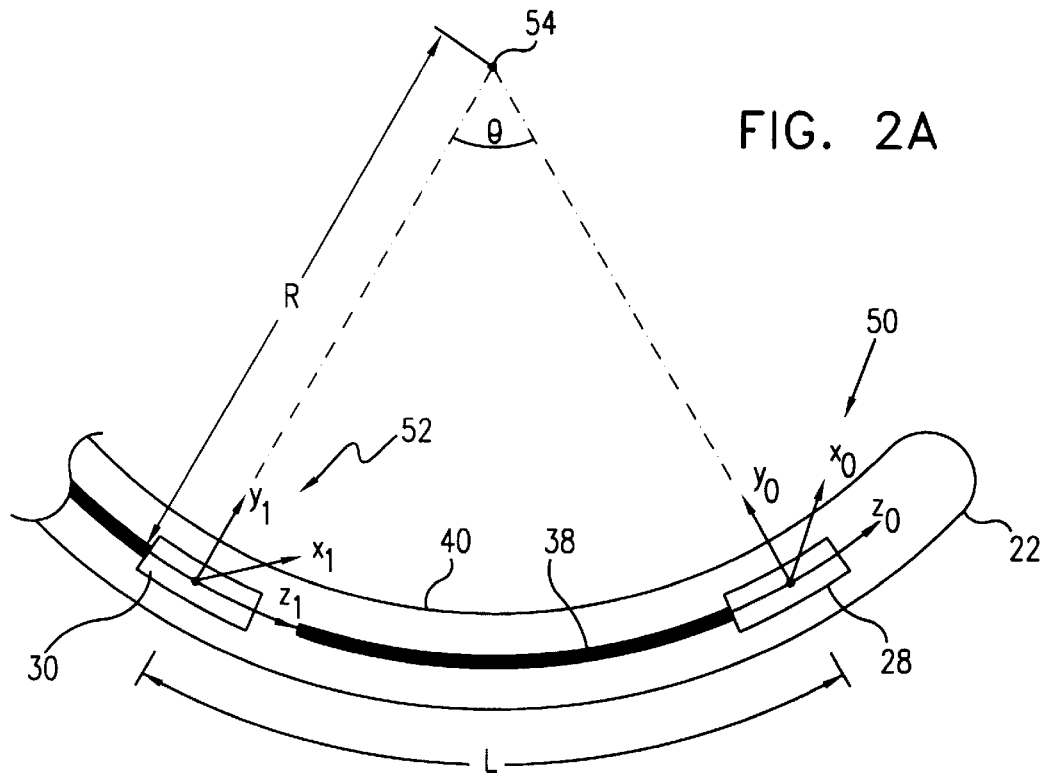
FIG. 2A is a schematic illustration of a portion of the catheter shown in FIG. 1, in a first, curved configuration.

FIG. 2A illustrates, for example, a case in which portion 40 of catheter 20 is bent in a plane, which we take to be the plane of the page without loss of generality. The length of portion 40 is taken to be L, as shown. Respective first and second local coordinate axes 50 ($x_o, y_o, z_o$) and 52 ($x_1, y_1, z_1$) are defined at the positions of first and second elements 28 and 30, wherein the local z-axis is taken in every case taken to be aligned with the longitudinal axis of catheter 20, generally parallel to member 38.

The six-dimensional position coordinates of first element 28 are determined and used to define the element's translational position and first local coordinate axes 50. The orientation coordinates of second element 30 define second local axes 52, which together with axes 50 determine a bend angle θ, as shown. An arc is thus defined having a radius of curvature given by R=L/θ, and a center of curvature 54 at a position y=R defined with respect to coordinate axes 50 or 52. The elasticity of member 38 ensures that portion 40 will generally follow this arc, so that the position of any point within portion 40 of catheter 20 may be conveniently determined.

FIG. 2B schematically illustrates the more general case, in which catheter 20 is free to twist in three dimensions. In the case shown here, portion 40 of catheter 20 has been twisted about its longitudinal axis by approximately 180°, so that axes $x_1$ and $y_1$ of second local axes 52 are oriented in generally opposite respective directions to axes $x_0$ and $y_0$ of local axes 50. The elasticity of member 38 causes portion 40 to assume a generally right-helical form, within the bounds of a cylinder 54 having a diameter $R_c$ and length d, as shown in the figure. The length d is defined by the translational displacement of element 30 relative to element 28, but determining $R_c$ generally requires solving an integral equation. Preferably, solutions to the equation are stored in the form of a look-up table, preferably within signal processing circuitry 36, as is known in the art. $R_c$ and d then determine the pitch of the helical form, so that the position of any point within portion 40 of catheter 20 may again be conveniently determined.

Preferably, portion 40 of catheter 20 will not be allowed to twist by more than 180° in either the clockwise or counterclockwise direction, so that the relative rotational coordinates of elements 28 and 30 will be unambiguous. If necessary, however, the twist of portion 40 may be continuously monitored, by analyzing the signals received from the elements, as catheter 20 is being inserted into and manipulated inside the body, so that rotations of greater than 180° will be detected. These greater twist angles are then used in appropriately determining $R_c$, as described above.

In the preferred embodiments described above, it is assumed that portion 40 of catheter 20 is free to move within a body cavity, and that the shape and configuration of portion 40 are determined substantially by its own elasticity. Portion 40 is caused to bend by a combination of a compressive axial force, generally exerted from proximal end 24 of catheter 20 by a user, such as a physician, and a lateral deflecting force exerted on distal end 22 by body tissue with which the distal end is in contact.

FIG. 3 schematically illustrates an alternative preferred embodiment of the present invention, in which catheter 20 bends controllably, not necessarily in an arcuate or helical form, by means of a steering mechanism 56. Preferably, mechanism 56 comprises an electronically- or mechanically-controlled deflection element, operating under the control of console 26, as described in the above-mentioned PCT patent application no. PCT/IL97/00159. Alternatively, mechanism 56 may comprise any suitable catheter steering or deflection device known in the art. Catheter 20 is sufficiently rigid, except in an immediate vicinity of mechanism 56, so as to bend only in the immediate vicinity of the mechanism. The position coordinates of elements 28 and 30 are used to measure the deflection angle θ, whereby the location of any point along portion 40 of catheter 20 may be determined. Preferably, the measured deflection angle is also used to provide feedback for closed-loop control of mechanism 56.

Figure 4:
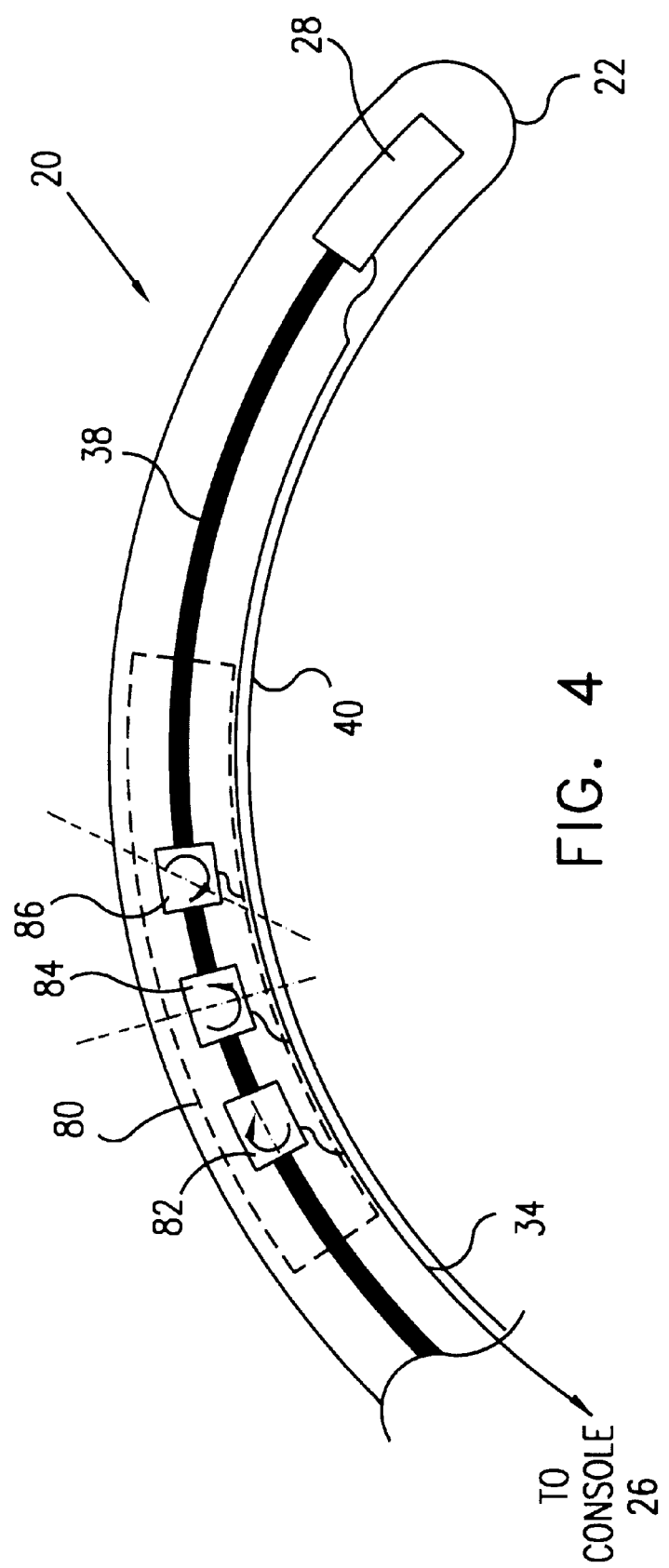
FIG. 4 is a schematic, partial, sectional illustration showing a bend-responsive catheter, in accordance with another preferred embodiment of the present invention.

FIG. 4 schematically illustrates another preferred embodiment of the present invention, which is similar to the embodiments described above except that in place of second position-sensing element 30, catheter 20 as shown here includes a bend sensor 80, responsive to the angle of bending of the catheter. Bend sensor 80 preferably comprises at least one piezoelectric element, or more preferably, three such elements 82, 84 and 86 as shown in the figure. The piezoelectric elements are mechanically coupled to resilient member 38, so that when member 38 is bent, as described above, the bending force is conveyed to and acts upon the elements. As is known in the art, the piezoelectric crystals generate voltage signals that are generally proportional to this bending force, which signals are conveyed by wires 34 to signal processing circuitry 36 in console 26.

Each of elements 82, 84 and 86 includes a piezoelectric crystal having a crystal axis aligned orthogonally to the axes of the other two elements, so that each crystal generates signals responsive to bending of catheter 20 about a different axis. Thus, as shown in FIG. 4, element 82 generates signals responsive to twisting of catheter 20 about its longitudinal axis, and elements 84 and 86 generate signals responsive to left-right and up-down bending, respectively.

Due to the generally constant elasticity of member 38, the signals generated by elements 82, 84 and 86 can be used to derive the bend and twist angles of portion 40 of catheter 20. These angles are taken together with the translational and orientational coordinates determined with respect to position-sensing element 28, in order to determine the positions of the plurality of points of interest along the length of catheter 20.

Other types of bend sensors may be used in place of sensor 80 shown in FIG. 4. For example, strain gauges may be substituted-for piezoelectric elements 82, 84 and 86. Such strain gauges have an electrical resistance that varies as a function of mechanical strain applied thereto, as is known in the art. Alternatively, fiberoptic sensors, as are known in the art, may be used to determine the bend angle of catheter 20, by measuring the loss and back-reflection of light conveyed through an optical fiber embedded in the catheter.

Furthermore, additional bend sensors of other types may be positioned at different locations along the length of catheter 20, so that multiple bends or bends of non-constant radius of curvature can be detected.

More generally speaking, while the preferred embodiments of the present invention have been described above with reference to one or two position-sensing elements 28 and 30 and a single bend sensor 80, it will be appreciated that for some applications, catheter 20 may preferably comprise a greater number of position sensors and/or of bend sensors. Such additional sensors may be particularly useful when a portion of the length of the catheter must be tracked within a convoluted passage, or when the catheter is brought to bear against and is desired to conform to a convoluted surface within a body cavity. Preferably, however, the number of such sensors is held to the minimum needed to achieve the desired accuracy of determination of the plurality of points along the length of the catheter.

Although for simplicity of illustration, catheter 20 has been shown and described above as comprising only the sensors and other elements necessary for the operation of the present invention, in preferred embodiments of the present invention, the catheter preferably includes other sensing and/or therapeutic devices, as are known in the art. The principles of the present invention may then be applied, for example, to map physiological activity or apply local therapeutic treatment within a body cavity, such as a chamber of the heart, with greater ease and accuracy than methods and devices known in the art.

It will be appreciated that the principles of the present invention may be applied, as well, to other flexible medical probes, such as endoscopes.

It will further be appreciated that the preferred embodiments described above are cited by way of example, and the full scope of the invention is limited only by the claims.

What is claimed is:

1. Invasive probe apparatus for use with an externally-applied magnetic field, the probe comprising:
   a flexible, elongate probe, having a distal portion adjacent to a distal end thereof, for insertion into the body of a subject, which portion assumes a predetermined, curved form when a force is applied thereto;
   a first sensor and a second sensor, fixed to the distal portion of the probe in known positions relative to the distal end, which sensors generate signals, the first sensor being a magnetic-field responsive sensor as a first position-sensing element for generating a first signal to enable determination of position and orientation coordinates of the first position-sensing element, said first signal defining a position and orientation coordinate signal, and the second sensor being a bend-sensing element for generating a second signal responsive to bending of the probe, said second signal defining a bend signal; and
   signal processing circuitry, which receives the position and orientation coordinate signal and the bend signal and processes them to find position and orientation coordinates of at least the first sensor and to determine the locations of a plurality of points along the length of the distal portion of the probe.

2. Apparatus according to claim 1, wherein the first sensor comprises three coils, which generate signals responsive to the externally-applied magnetic field.

3. Apparatus according to claim 1, wherein the probe has a generally constant elasticity over the length of the distal portion thereof.

4. Apparatus according to claim 1, wherein the probe comprises a resilient longitudinal member.

5. Apparatus according to claim 4, wherein the bend-sensing element generates signals responsive to a direction of bending of the probe.

6. Apparatus according to claim 4, wherein the bend-sensing element comprises at least one piezoelectric crystal.

7. Apparatus according to claim 6, wherein the at least one piezoelectric crystal comprises three such crystals, each crystal having an axis, wherein the axes are mutually orthogonal.

8. Apparatus according to claim 4, wherein the bend-sensing element comprises a fiberoptic sensor.

9. Apparatus according to claim 4, wherein the bend-sensing element comprises a strain sensor.

10. Apparatus according to claim 4, wherein the signal processing circuitry determines a radius of curvature of the probe.

11. Apparatus according to claim 4, wherein the signal processing circuitry determines a radius and a pitch of a helical form described by the probe.

12. Apparatus according to claim 4, wherein the probe comprises a deflection device within the distal portion thereof.

13. Apparatus according to claim 1, wherein the second sensor comprises a magnetic-field responsive sensor as a second position-sensing element.

14. Apparatus according to claim 13, wherein the signal processing circuitry processes the signals generated by the second sensor to find position and orientation coordinates thereof.

15. Apparatus according to claim 14, wherein the position and orientation coordinates found by the signal processing circuitry comprise six-dimensional position and orientation coordinates.

16. A method for determining the course of an elongate, flexible probe inside the body of a subject through the use of an externally-applied magnetic field, comprising:
   generating an externally-applied magnetic field;
   finding position and orientation coordinates of a point on the probe using at least one magnetic field responsive sensor on the probe;
   measuring a bending angle of a portion of the probe adjacent to the point; and
   processing the position and orientation coordinates and the bending angle to determine the locations of a plurality of points along the length of a portion of the probe inside the body.

17. A method according to claim 16, wherein finding position and orientation coordinates comprises finding six-dimensional position and orientation coordinates.

18. A method according to claim 16, wherein measuring a bending angle comprises finding position coordinates of an additional point on the probe.

19. A method according to claim 16, wherein measuring a bending angle comprises measuring a force associated with bending the probe.

20. A method according to claim 19, wherein processing the position coordinates and the bending angle comprises calculating a radius of curvature of the probe.

21. A method according to claim 19, wherein processing the position coordinates and the bending angle comprises calculating a radius of a helical path described by the probe.

22. A catheter comprising:
   an elongated member;
   a proximal position sensor on a distal end of the member;
   a distal position sensor on the distal end and spaced a distance from the proximal position sensor, the proximal position sensor and the distal position sensor generating signals to enable determination of position coordinates of the proximal position sensor and the distal position sensor respectively; and
   a bend portion between the proximal position sensor and the distal position sensor, wherein position coordinates of the proximal position sensor and the distal position sensor are used to determine a radius of curvature for the bend portion, the radius of curvature defining an arc and the bend portion following the arc upon a bending of the bend portion such that a position of any point on the bend portion can be determined.

23. The catheter according to claim 22, wherein at least one of the proximal position sensor and the distal position sensor is a magnetic field sensor.

24. The catheter according to claim 22, wherein at least one of the proximal position sensor and the distal position sensor is an acoustic sensor.

25. The catheter according to claim 22, wherein at least one of the proximal position sensor and the distal position sensor is an electrical sensor.

26. The catheter according to claim 22, further comprising a physiological sensor.

27. The catheter according to claim 26, further comprising a therapeutic device.

28. The catheter according to claim 27, wherein at least one of the proximal position sensor and the distal position sensor is a magnetic field sensor.

29. The catheter according to claim 27, wherein at least one of the proximal position sensor and the distal position sensor is an acoustic sensor.

30. The catheter according to claim 27, wherein at least one of the proximal position sensor and the distal position sensor is an electrical sensor.

* * * * *

UNITED STATES PATENT AND TRADEMARK OFFICE
CERTIFICATE OF CORRECTION

PATENT NO. : 6,272,371 B1  
DATED : August 7, 2001  
INVENTOR(S) : Ben-Haim, Shlomo Page 1 of 1

It is certified that error appears in the above-identified patent and that said Letters Patent is hereby corrected as shown below:

<u>Title page,</u>
[12] United States Patent
    Shlomo
should be:

[12] United States Patent
    Ben-Haim

[75] Inventor: Ben-Haim Shlomo should be:

[75] Inventor: Ben-Haim, Shlomo

Signed and Sealed this

Twenty-ninth Day of January, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,272,371 B1  Page 1 of 1
APPLICATION NO. : 09/125932
DATED : August 7, 2001
INVENTOR(S) : Shlomo Ben-Haim It is certified that error appears in the above-identified patent and that said Letters Patent is hereby corrected as shown below:

On the Title Page;
Item [12] United States Patent
     Shlomo

Should be:

[12] United States Patent
     Ben-Haim

Item [75] Inventor: Ben-Haim Shlomo

Should be:

[75] Inventor: Ben-Haim, Shlomo

Signed and Sealed this

Third Day of March, 2009

JOHN DOLL
*Acting Director of the United States Patent and Trademark Office*